United States Patent [19]

Appelgren et al.

[11] Patent Number: 5,001,161

[45] Date of Patent: Mar. 19, 1991

[54] PHARMACEUTICAL COMPOSITION COMPRISING METROPROLOL SUCCINATE

[75] Inventors: Curt H. Appelgren, Kungsbacka; Eva C. Eskilsson, Mölnlycke, both of Sweden

[73] Assignee: Aktiebolaget Hassle, Molndal, Sweden

[21] Appl. No.: 172,897

[22] Filed: Mar. 25, 1988

Related U.S. Application Data

[63] Continuation-in-part of Ser. No. 690,197, Jan. 10, 1985, Pat. No. 4,780,318.

[30] Foreign Application Priority Data

Jan. 10, 1984 [SE] Sweden .................. 8400085

[51] Int. Cl.⁵ .................. A61K 31/045; A61K 31/19; A61K 31/20
[52] U.S. Cl. .................. 514/651; 514/652; 424/469
[58] Field of Search .................. 424/469; 514/651, 652

[56] References Cited

U.S. PATENT DOCUMENTS

| | | | |
|---|---|---|---|
| 3,483,221 | 12/1969 | Wilhelm | 564/360 |
| 3,873,600 | 3/1975 | Brandstrom et al. | 568/565 |
| 3,996,382 | 12/1976 | Berntsson et al. | 514/651 |
| 4,256,752 | 3/1981 | von Bebenburg et al. | 514/925 |
| 4,258,062 | 3/1981 | Jonas et al. | 514/652 |
| 4,341,759 | 7/1982 | Bogentoft et al. | 424/417 |
| 4,578,075 | 3/1986 | Urquhart et al. | 424/453 |
| 4,615,697 | 10/1986 | Robinson | 424/428 |
| 4,627,850 | 12/1986 | Deters et al. | 424/457 |
| 4,681,583 | 7/1987 | Urquhart et al. | 424/453 |

FOREIGN PATENT DOCUMENTS

| | | |
|---|---|---|
| B322506 | 4/1970 | Sweden . |
| B384853 | 5/1976 | Sweden . |
| B385693 | 7/1976 | Sweden . |
| B388849 | 10/1976 | Sweden . |
| B402765 | 7/1978 | Sweden . |
| B422052 | 2/1982 | Sweden . |
| B441827 | 11/1985 | Sweden . |
| 1492647 | 11/1977 | United Kingdom . |
| 1524036 | 9/1978 | United Kingdom . |

*Primary Examiner*—Ronald W. Griffin
*Attorney, Agent, or Firm*—White & Case

[57] ABSTRACT

The present invention relates to metoprolol succinate, a new therapeutically active compound, and pharmaceutical preparations comprising this new compound.

1 Claim, No Drawings

PHARMACEUTICAL COMPOSITION COMPRISING METROPROLOL SUCCINATE

This application is a continuation-in-part of application Ser. No. 690,197, filed Jan. 10, 1985, now U.S. Pat. No. 4,780,318.

TECHNICAL FIELD

The present invention relates to a new oral, therapeutically active compound, which can be released in the gastrointestinal tract below the upper part of the small intestine.

The object of the present invention is to obtain a therapeutically active compound intended to be released close to or within the colon, and particularly to such active compounds which are soluble in the pH range 1 to 8.

BACKGROUND OF THE INVENTION

There exists an everlasting problem within pharmacy to be able to administer a therapeutically active compound as close as possible to the colon, or preferably in the colon in order to thereby to eliminate the risk for acidic influence on the active compound by the gastric juice, or to prevent from irritation of the ventricular mucous membrane due to a reflux, or to obtain a therapeutical effect in the lower part of the gastrointestinal tract.

As suitable active compounds it has previously been proposed propanolol, alprenolol, and metoprolol tartrate, quinidine sulphate, quinidine bisulphate, quinidine hydrochloride, furosemide, and 5aminosalicylic acid, i.e., such weak bases or salts thereof, the pH of which is 1 to 8.

DESCRIPTION OF THE PRESENT INVENTION

It has now surprisingly been shown possible to be able to use, for this purpose, a previously unknown compound, viz. metoprolol succinate.

The metoprolol succinate has a melting point of 136°–137° C.

This compound can, in order to be administered orally be treated in accordance with the method proposed in EP-A1-0 040 590. Herein it has been proposed an oral pharmaceutical composition comprising a core containing a therapeutically active compound, which core has been coated with a layer comprising 10 to 85% by weight of an anionic polymer soluble at a pH above 5.5, and 15 to 90% by weight of a waterinsoluble polymer selected from the group of quaternary ammonium substituted acrylic polymers.

From the point of view of flavor and/or identification a flavoured or coloured layer can optionally be applied outside the release controlling layer. This is, however, no part of the present invention.

When dosing the ready made product a number of discrete, coated particles/granules corresponding to a therapeutical dose unit of the actual therapeutical compound is administered.

When administering, in order to achieve a steady blood plasma level of the therapeutically active compound, a split dose unit of the therapeutically active compound provided with a coating according to the present invention can be administered together with some particles/granules which are not coated.

The particles are normally packed in small envelopes, tubular containers, or other capsules comprising a dose unit of a therapeutically active compound.

We claim:

1. A pharmaceutical composition comprising metoprolol succinate together with a sustained release pharmaceutically acceptable carrier.

* * * * *

Disclaimer

5,001,161 — Curt H. Appelgren, Kungsbacka; Eva C. Eskilsson, Molnlycke, both of Sweden. PHARMACEUTICAL COMPOSITION COMPRISING METROPROLOL SUCCINATE. Patent dated March 19, 1991. Disclaimer filed Jan. 26, by the Assignee, AstraZeneca Limited Partnership.

The term of this patent, subsequent to the term of patent number 4,947,745 has been disclaimed.

*(Official Gazette May 10, 2005)*

UNITED STATES PATENT AND TRADEMARK OFFICE
CERTIFICATE OF CORRECTION

PATENT NO. : 5,001,161
DATED : March 19, 1991
INVENTOR(S) : Curt H. Appelgren et al.

It is certified that error appears in the above-identified patent and that said Letters Patent is hereby corrected as shown below:

Column 2,
Line 36, "A pharmaceutical" should read -- A sustained release pharmaceutical --.
Line 37, "a sustained release" should read -- a --.

Signed and Sealed this

Sixth Day of September, 2005

JON W. DUDAS
*Director of the United States Patent and Trademark Office*